United States Patent [19]

Ansourian et al.

[11] Patent Number: 5,500,004
[45] Date of Patent: Mar. 19, 1996

[54] CARDIO MYOSTIMULATION SYSTEM WITH DEFIBRILLATION

[75] Inventors: Megeurditch N. Ansourian; Peter M. Nickolls, both of Sydney, Australia

[73] Assignee: Telectronics Pacing Systems, Inc., Englewood, Colo.

[21] Appl. No.: 336,189

[22] Filed: Nov. 8, 1994

[51] Int. Cl.⁶ ................................................. A61N 1/368
[52] U.S. Cl. .................... 607/4; 607/6; 600/17
[58] Field of Search .................. 607/2–12; 128/673, 128/668

[56] References Cited

U.S. PATENT DOCUMENTS

| | | | |
|---|---|---|---|
| 4,796,630 | 1/1989 | Regna | 128/419 |
| 5,178,140 | 1/1993 | Ibrahim | 128/419 |
| 5,215,083 | 6/1993 | Drane et al. | 128/419 |
| 5,251,621 | 10/1993 | Collins | 607/4 |
| 5,390,679 | 2/1995 | Martin | 128/673 |

Primary Examiner—Angela D. Sykes
Assistant Examiner—Stephen Huang
Attorney, Agent, or Firm—Gottlieb, Rackman & Reisman

[57] ABSTRACT

A pacemaker system for a heart having an external muscle is used to control pacing of the heart during normal or even arrhythmic modes. In these modes, the muscle is stimulated synchronously with the heart to augment the heart's cardiac functions. When the heart undergoes ventricular fibrillation, the muscle is provided with a signal to cause the muscle to contract and expel blood from the heart chambers. Defibrillation shock is then applied to the heart to halt the fibrillation. The system is rendered more effective, safer and uses less power because the defibrillating energy is efficiently transferred to the heart muscles and not to the blood contained in its chambers. The system includes a microprocessor, muscle stimulating circuitry, defibrillation circuitry and an interface for exchanging signals between the microprocessor and the remaining components.

20 Claims, 6 Drawing Sheets

CARDIO MYOSTIMULATION SYSTEM WITH DEFIBRILLATION

BACKGROUND OF THE INVENTION

1. Field of Invention

This invention relates to a combined muscle stimulation, pacing and defibrillation apparatus and its method of operation for detecting abnormalities of a patient's heart and, in response to such detection, administering defibrillation therapy. More particularly, this invention relates to a pacing apparatus and method that employs defibrillation therapy which comprises the coordination, control and generation of stimulation pulses to both the patient's heart and to a muscle graft that has been previously wrapped around the heart, with means being provided to insure that the defibrillation therapy is most efficient achieved.

2. Description of the Prior Art

Severe chronic cardiac insufficiency arising from cardiac disease or injury shortens and degrades the quality of life of many patients. One form of severe chronic cardiac insufficiency, congestive heart failure, is a pathophysiological state in which cardiac output is inadequate to meet physiological requirements of the body. The mortality rate for congestive heart failure is greater than 50% within 5 years of onset. Treatments for severe chronic cardiac insufficiency include heart transplants, artificial heart implants and cardiomyoplasty. Cardiac transplantation, using cyclosporine to inhibit tissue rejection, is a very successful technique for prolonging a cardiac patient's life, improving the survival rate to 80% at 1 year. However, the transplant operation is very expensive and heart availability is limited. The artificial heart has had very limited success.

Dynamic cardiomyoplasty is a surgical and electrical therapeutic technique used to overcome or at least alleviate cardiac insufficiency. This technique consists of using a skeletal muscle flap which is dissected from a patient, while maintaining its neural tissues and neurovascular structures, surgically placed around the patient's heart. An electrical stimulation device, with an electrical pulse generator and intramuscular electrodes, is implanted for performing muscle electrical stimulation in synchrony with ventricular systole to support cardiac pumping.

Repeated stimulation of the skeletal muscle transforms it into a fatigue-resistant muscle suitable for chronic ventricular assistance, enabling dynamic cardiomyoplasty. The skeletal muscle is then trained to function so as to assist cardiac muscle to increase the patient's cardiac output. Sequential and progressive skeletal muscle electrical stimulation causes glycolytic muscle fibers, predominant in skeletal muscle, to take the form of oxidative fibers. Oxidative fibers are resistant to fatigue and have histochemical and biochemical characteristics of myocardium.

Presently, cardiomyoplasty patients suffering from ventricular fibrillations are treated by one of several methods, depending on the circumstances at the time of the onset of fibrillation. Each of these methods has several disadvantages. Ventricular fibrillations occurring in the hospital must be first confirmed by doctors or paramedical personnel. Standard high energy defibrillation shocks are then applied to the patient. Of course, these shocks must be applied by people having special training. If the ventricular fibrillation occurs outside a hospital, the patient must wait for trained medical help to arrive and apply the high energy shocks as discussed above.

Commonly assigned U.S. Pat. No. 5,251,621, incorporated herein by reference, proposes a therapy for preventing and terminating cardiac arrhythmias which may lead to ventricular fibrillation and sudden death in patients suffering from congestive heart failure. The proposed therapy combines antiarrhythmic pacing of various forms with skeletal muscle graft stimulation. Muscle graft stimulation increases cardiac output, aortic pressure and, therefore, perfusion of the heart to alleviate myocardial ischemia and ameliorate arrhythmias. The device performs pacing, defibrillation and skeletal muscle stimulation is disclosed in commonly assigned U.S. Pat. No. 5,251,621. However this patent only teaches the stimulation of the skeletal muscle in synchronism with arrhythmia pacing in order to increase cardiac output.

Commonly assigned U.S. Pat. Nos. 4,796,630; 5,178,140; and 5,215,083 disclose devices performing both pacing and defibrillating functions. None of the cited references disclose, or even suggest, a device capable of performing defibrillation therapy which includes the stimulation of the skeletal muscle as part of the therapy.

OBJECTIVES AND SUMMARY OF THE INVENTION

An objective is to provide a defibrillation method and apparatus which requires defibrillation shocks of lower amplitude than in prior art devices resulting in a safer procedure and reduced power consumption.

A further objective is to provide a method and apparatus for performing a defibrillation function for a cardiomyoplasty patient efficiently by the stimulation of a skeletal muscle disposed about the heart.

Yet another objective is to provide a combined apparatus for performing a plurality of cardiac functions including normal rate responsive pacing, arrhythmic pacing for terminating arrhythmia, cardiac pumping assisted by cardiomyoplasty and effective low power defibrillation. Other objectives and advantages of the invention shall be provided in the following description.

The present inventors have realized that a problem with existing defibrillation therapies is that they require large electric defibrillation shocks to compensate for dissipation of the shocks in the blood contained in the heart. This problem is resolved in the present invention by providing a time period just prior to the application of defibrillation shocks, during which the skeletal muscle is stimulated to cause the muscle to contract around the heart and thereby eject the blood contained in the heart's chambers.

Briefly, in accordance with the principles of the present invention, a pacemaker system is provided for stimulating a patient's heart. The patient is also provided with a skeletal muscle grafted onto the heart to assist its cardiac functions. The pacemaker system includes means for analyzing signals from the heart for detecting, classifying and correcting abnormal episodes or conditions of the heart such as arrhythmia. The pacemaker system further includes heart stimulating means for generating and delivering stimulating pulses of various amplitudes to the heart. These stimulating means may include pacing electrodes, as well as defibrillating electrodes, receiving the various pulses. These pulses may be characteristic of standard pacemaker stimulation, cardioversion or defibrillation shocks. The pacemaker system also includes at least one muscle stimulation electrode which is adapted to be placed in electrical contact with the muscle graft. This electrode receives muscle stimulating pulses from a muscle pulse stimulating means. During the normal mode of operation the muscle pulse stimulating means generates stimulating pulse trains which are delivered to the muscle and have an amplitude, duration and frequency to effect a desired contraction of the muscle for assisting the heart in its cardiac functions. Importantly in this mode, the muscle stimulating pulses are synchronized with the natural or paced periodic heart contractions.

In response to the detection of an abnormal condition of the heart, such as a ventricular fibrillation, the pacemaker system activates muscle stimulation and fibrillation control means which controls and synchronizes operations of the heart stimulating means and the muscle pulse stimulating means to apply a defibrillation therapy. During this therapy, the skeletal muscle is stimulated first to expel blood from the heart chambers and then defibrillation shocks are applied to the heart. In addition, the device is also adapted to perform other therapeutic functions to correct other such as arrhythmia, ventricular tachycardia, and so on. In these modes of operations, pacing and muscle stimulation are combined synchronously corresponding to the classification of abnormal condition determined by a detecting and classifying means.

DETAILED DESCRIPTION OF THE INVENTION

Figure 1:
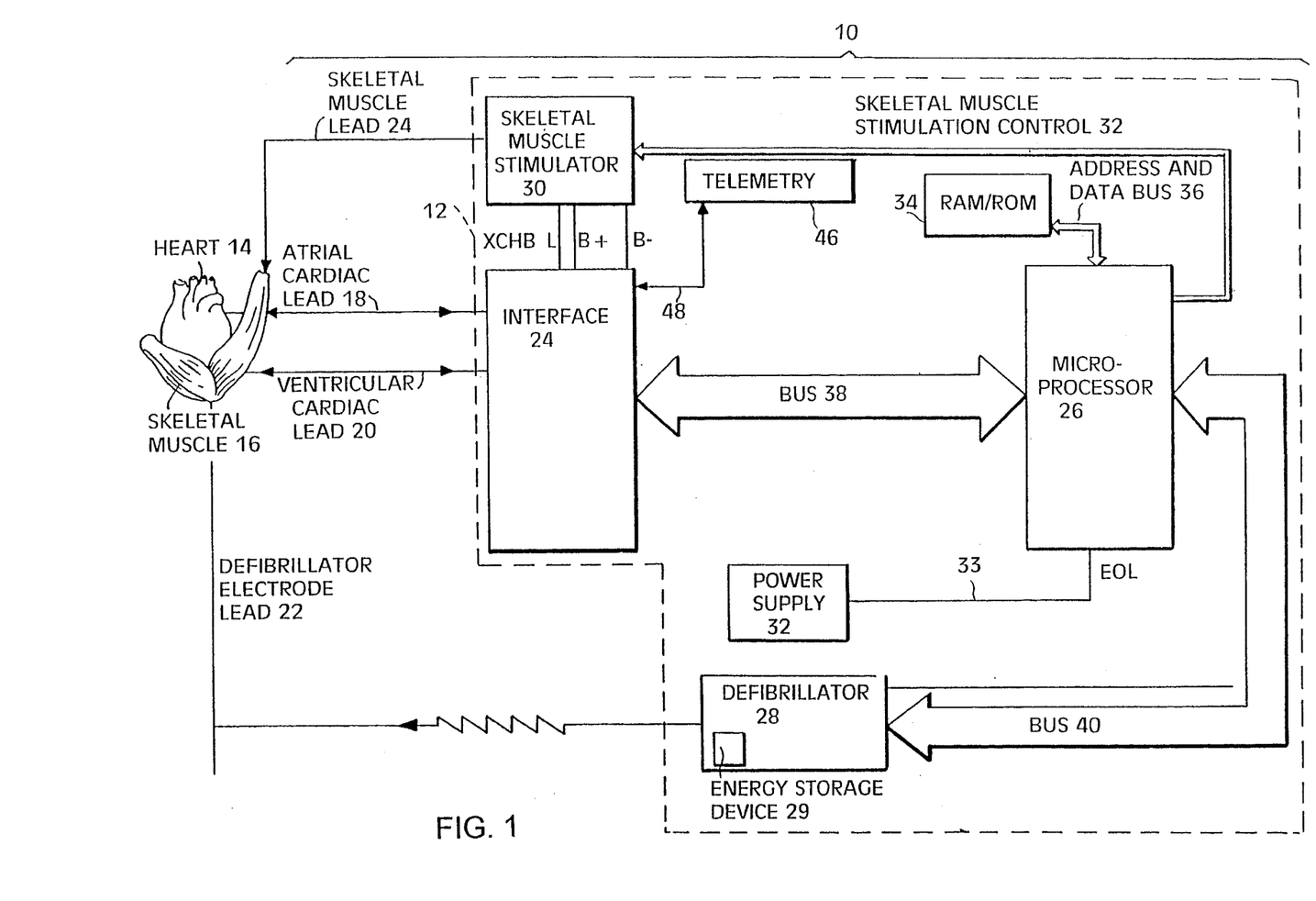
FIG. 1 is a block diagram of an implanted pacemaker system constructed in accordance with this invention, including a rate-responsive, dual chamber arrhythmia control system.

In FIG. 1 there is depicted a block diagram of a pacemaker system 10. The system 10 is designed to be implanted within a patient and includes a pulse module or pacemaker 12 and leads for connecting module 10 to a patient's heart 14 and skeletal muscle 16. These leads include an atrial cardiac lead 18, a ventricular cardiac lead 20 extending to the atrium and the ventricle of the patient's heart 14, respectively, as well as a defibrillation electrode lead 22 and a skeletal muscle lead 23.

The pulse module 12 generally includes an interface 24, a microprocessor 26, a defibrillator 28, a skeletal muscle simulator 30 and a power supply 32. The interface 24 is provided for the detection of analog signals representing cardiac electrical activity and for the delivery of pacing pulses to the heart over leads 18 and 20. The microprocessor 26, in response to various inputs received from the interface 24 as well as from a defibrillator 28, performs various operations so as to generate different control and data outputs to pacemaker interface 24, skeletal muscle stimulator 30 and defibrillator 28. The power supply 32 provides reliable voltage to the other components of the pulse module. When the power supply 32 is nearly exhausted it generates an End-Of-Life (EOL) signal on line 33 to the microprocessor 26.

Skeletal muscle stimulator 30 generates electrical pulses on a skeletal muscle lead 23 for stimulating the skeletal muscle 16. The pulses to muscle 16 are generated according to timed control signals from microprocessor 26 received via skeletal muscle stimulation control bus 32.

The defibrillator 28 has an energy storage device 29 which may consist of one or more capacitors (not shown), and is used to produce high voltage pulses responsive to control signals from microprocessor 26 received on bus 40. The defibrillator electrode lead 22 transmits the defibrillator shocks from the implanted pacemaker 12 to the heart 14.

The microprocessor 26 is connected to a Random Access/ Read Only memory unit 34 by an address and data bus 36.

The pacemaker 12 also includes a telemetry circuit 46 over which control signals and cardiac signals can be exchanged with the outside world. The telemetry circuit 46 is coupled to interface 24 by a bus 48.

As more fully described below, microprocessor 26 and interface 24 are connected by a data and communication bus 38 for exchanging various data.

Microprocessor 26 transmits control signals, according to the description below, over skeletal muscle stimulation control bus 32 to the skeletal muscle stimulator 30. As also more fully described below, microprocessor 26 is connected to defibrillator 16 by a bus 40.

Figure 2:
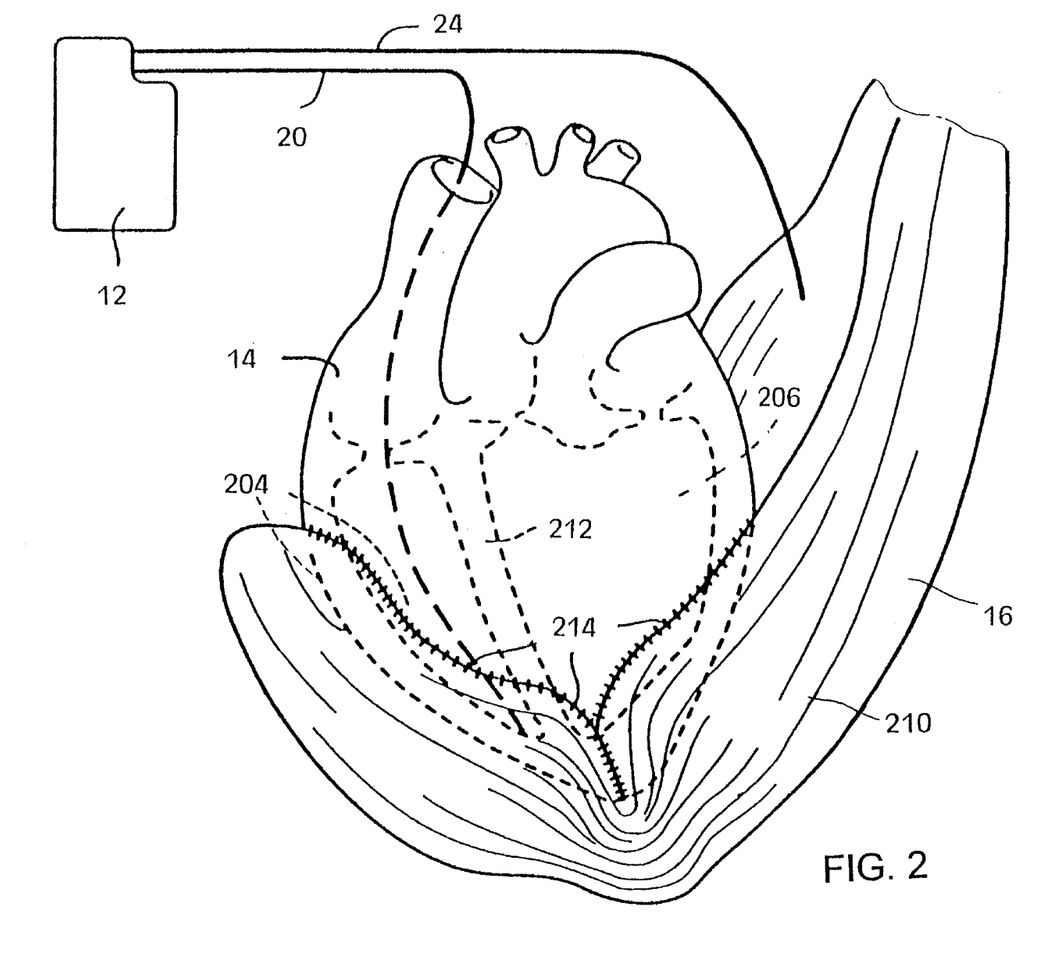
FIG. 2 shows a somewhat simplified side elevational view of a heart enveloped in a skeletal muscle and provided with the pacemaker system of FIG. 1.

FIG. 2 illustrates an example of a cardiac assist arrangement 200 for performing cardiac pacing, long-term stimulation of skeletal muscles using systolic augmentation, and defibrillation of the heart. A latissimus dorsi skeletal muscle 16 is positioned over the right ventricle 204 and left ventricle 206 of a patient's heart 14. The longitudinal fibers 210 of the latissimus dorsi are oriented generally parallel to the longitudinal axes of the ventricles 204 and 206 and interventricular septum 212 of the heart. The skeletal muscle 16 is positioned in this manner so that when it is stimulated, it compresses the ventricles, particularly the left ventricle 206, and augments the force of right and left ventricular contractions.

The ventricular cardiac lead 20 is implanted in the heart's right ventricle 204 and the skeletal muscle lead 24 extends from the muscle stimulator 30 (shown in FIG. 1) to the latissimus dorsi muscle 16. The skeletal muscle lead 24 may be placed directly on a nerve or placed near nerve branches within the latissimus dorsi muscle 16 to provide for selective depolarization of intact motor nerve fibers. In this manner the muscle 16 is forced selectively to contract about the heart 14, for either systolic augmentation or defibrillation.

Details of the interface 24 and its method of operation are found in U.S. Pat. No. 5,251,621 discussed above and incorporated herein by reference.

Figure 3:
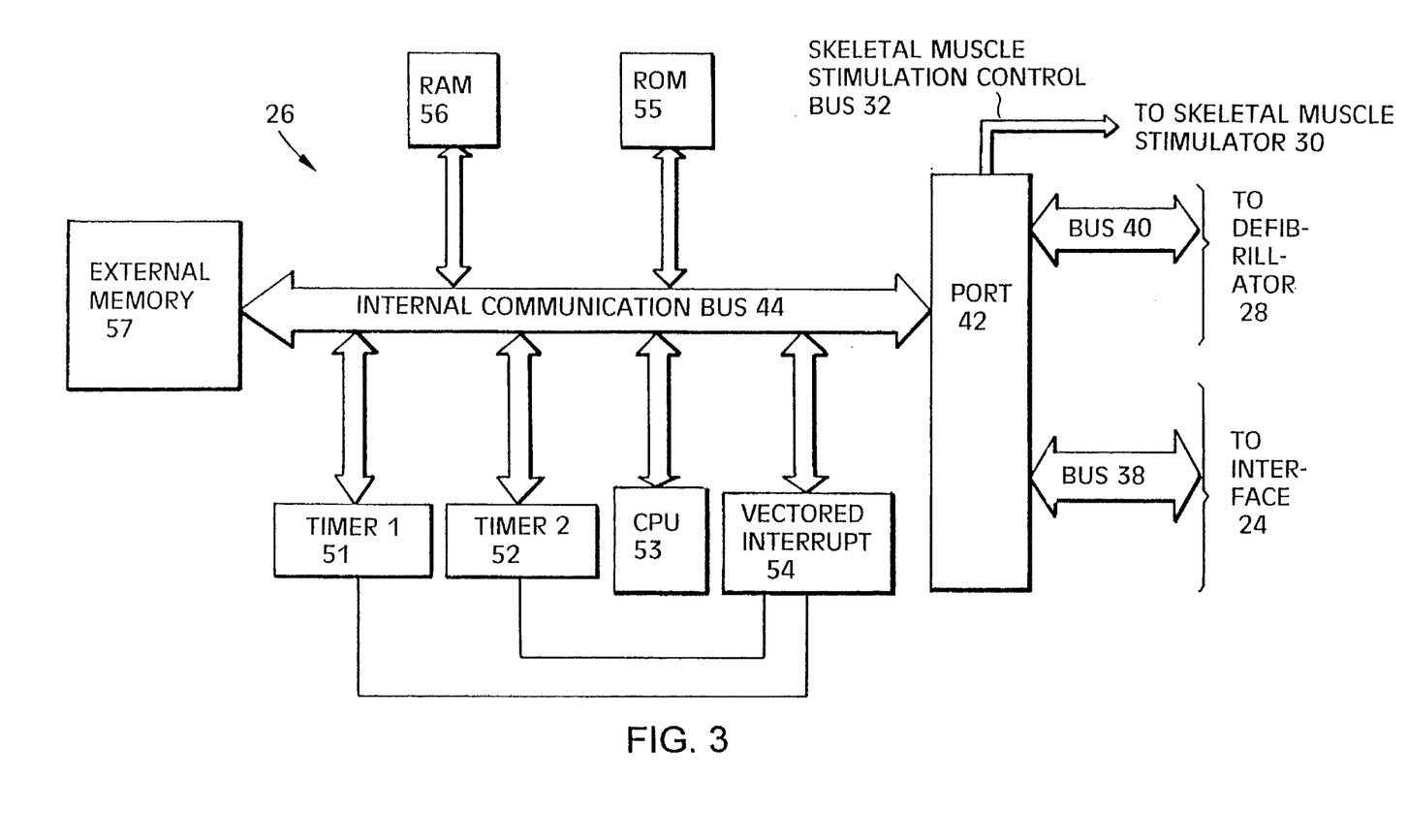
FIG. 3 shows a block diagram of the microprocessor of the pacemaker system of FIG. 3.

Referring to FIG. 3, microprocessor 26 comprises two timers 51 and 52, a CPU 53, a vectored interrupts block 54, a ROM 55, a RAM 56, an external memory 57, a port 42 and an internal communications bus 44. RAM 56 acts as a scratch pad and active memory during execution of the various programs stored in ROM 55 and used by microprocessor 26. These programs include system supervisory programs, detection algorithms for detecting and confirming various arrhythmias, and programming for implementing the flow chart of FIG. 4 as well as storage programs for storing, in external memory 57, data concerning the functioning of module 12 and the electrogram provided by ventricular cardiac lead 20 (FIG. 1). Timers 51 and 52, and associated control software, implement timing functions required by microprocessor 26.

Microprocessor 26 receives various status and control inputs from the interface 24 and defibrillator 16 on buses 38 and 40 and produces the control signals on these buses and bus 32 necessary for various functions including normal rate responsive pacing of the atria and/or ventricle, skeletal muscle stimulation and defibrillation.

More specifically, the atrial and ventricular pace control inputs derived from the signals received from the heart on leads 18 and 20 determine the respective types of atrial and/or ventricular pacing to be delivered to the heart. Details of this function are described in commonly assigned U.S. Pat. No. 4,869,252 to Norma Louise Gilli, issued Sep. 26, 1989, and entitled "Apparatus And Method For Controlling Pulse Energy In Antitachyarrhythmia And Bradycardia Pacing Devices," which description is incorporated herein by reference.

The skeletal muscle stimulator 30 shown in FIG. 1, receives input signals from microprocessor 26 over the skeletal muscle stimulation control bus 32. In addition, the interface 24 supplies to stimulator 30 battery power over two battery leads B+ and B− which provide energy for biphasic skeletal muscle stimulation. The battery leads B+, B− are floating with respect to the power supplied by supply 32 to provide signal isolation. The signal XCHB L is a cross channel blanking control signal used to disable cardiac sensing by the interface 24 during generation of a skeletal muscle stimulation pulse. Therefore this signal prevents the microprocessor 26 from incorrectly classifying a skeletal muscle stimulation pulse as an episode of intrinsic cardiac activity. Details of the skeletal muscle stimulator are provided in commonly assigned U.S. Pat. No. 5,251,621, incorporated herein by reference.

Figure 4A:
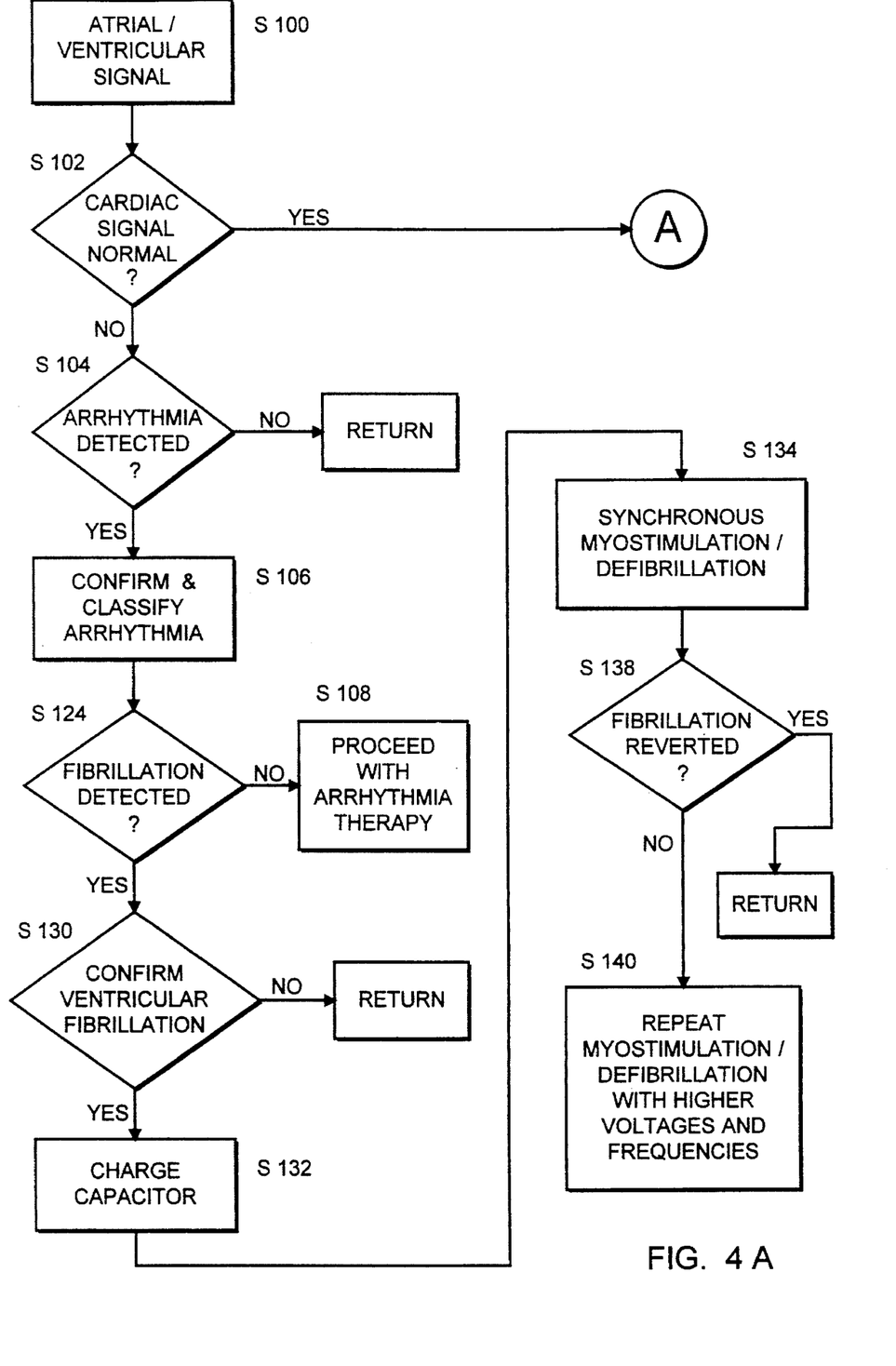
FIGS. 4A and 4B show flow charts for the operation of the pacemaker system of FIG. 1.
Figure 4B:
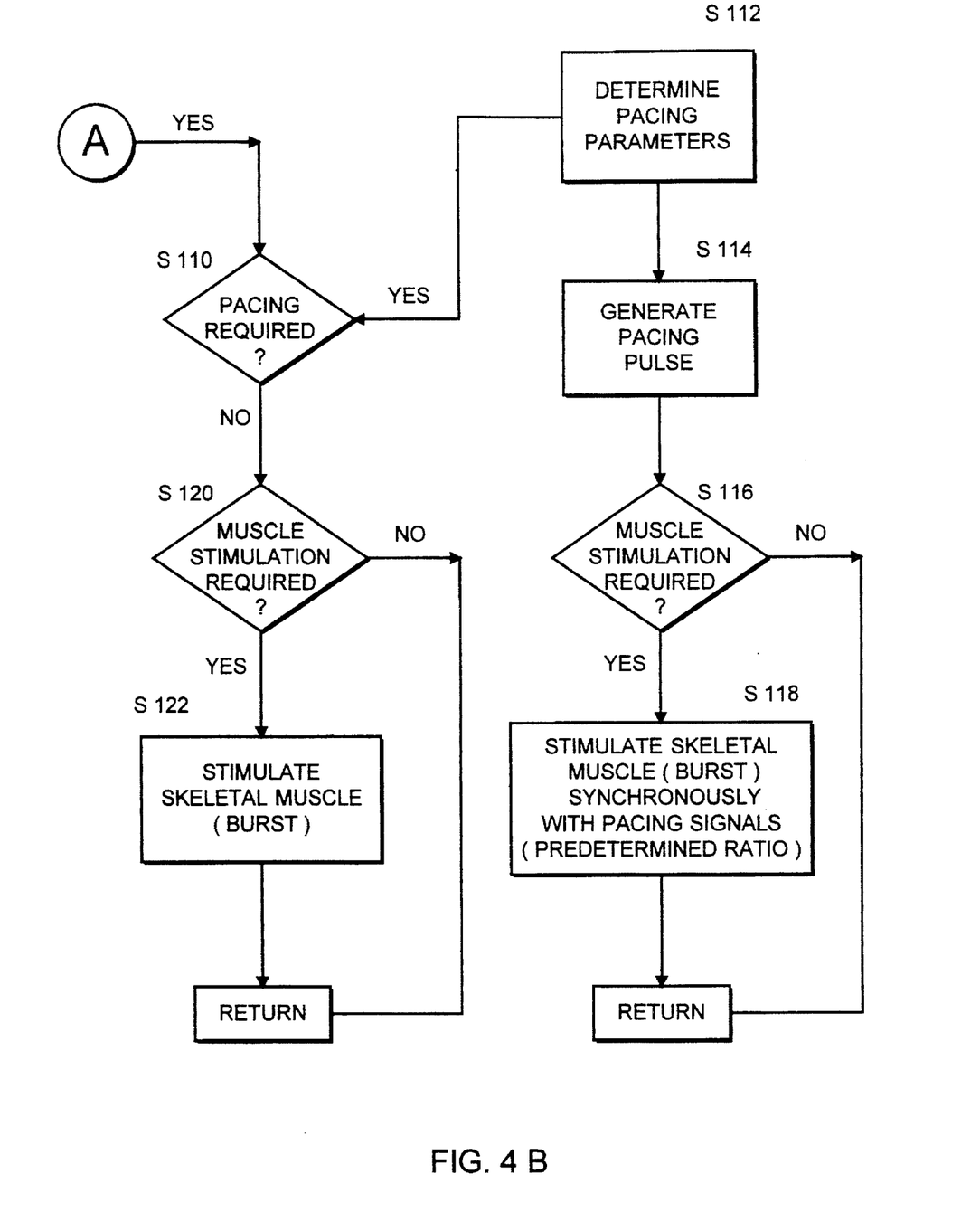

The operation of the pacemaker system 10 is now described in conjunction with the flow charts of FIGS. 4A and 4B. In step S100, the microprocessor receives and analyzes signals form the atrial and ventricle leads. In step S102, the microprocessor determines from these signals whether the cardiac function of heart 14 is normal, i.e. whether corrective therapy is required.

If the cardiac function is normal, the microprocessor determines in step S110 whether the pacing is required. If pacing is required, in step S112 the microprocessor enters a pacing mode wherein it determines the pacing parameters, and in step S114 the pacing signals are generated for atrial and/or ventricle pacing. In step S116 the microprocessor determines if skeletal muscle stimulation is required. Skeletal muscle stimulation signals are generated by the microprocessor in step S118, which signals are synchronous with the pacing signals generated in step S114. These signals are applied to the muscle 16 to augument the functions of the heart.

Going back to step S110, if pacing is not required, in step S120, the microprocessor determines if skeletal muscle stimulation is beneficial for augmenting the patient's cardiac functions. If skeletal muscle stimulation is required, than in step S122 the microprocessor generates muscle stimulating signals synchronous with the intrinsic or natural heart beat of the patient.

Figure 5:
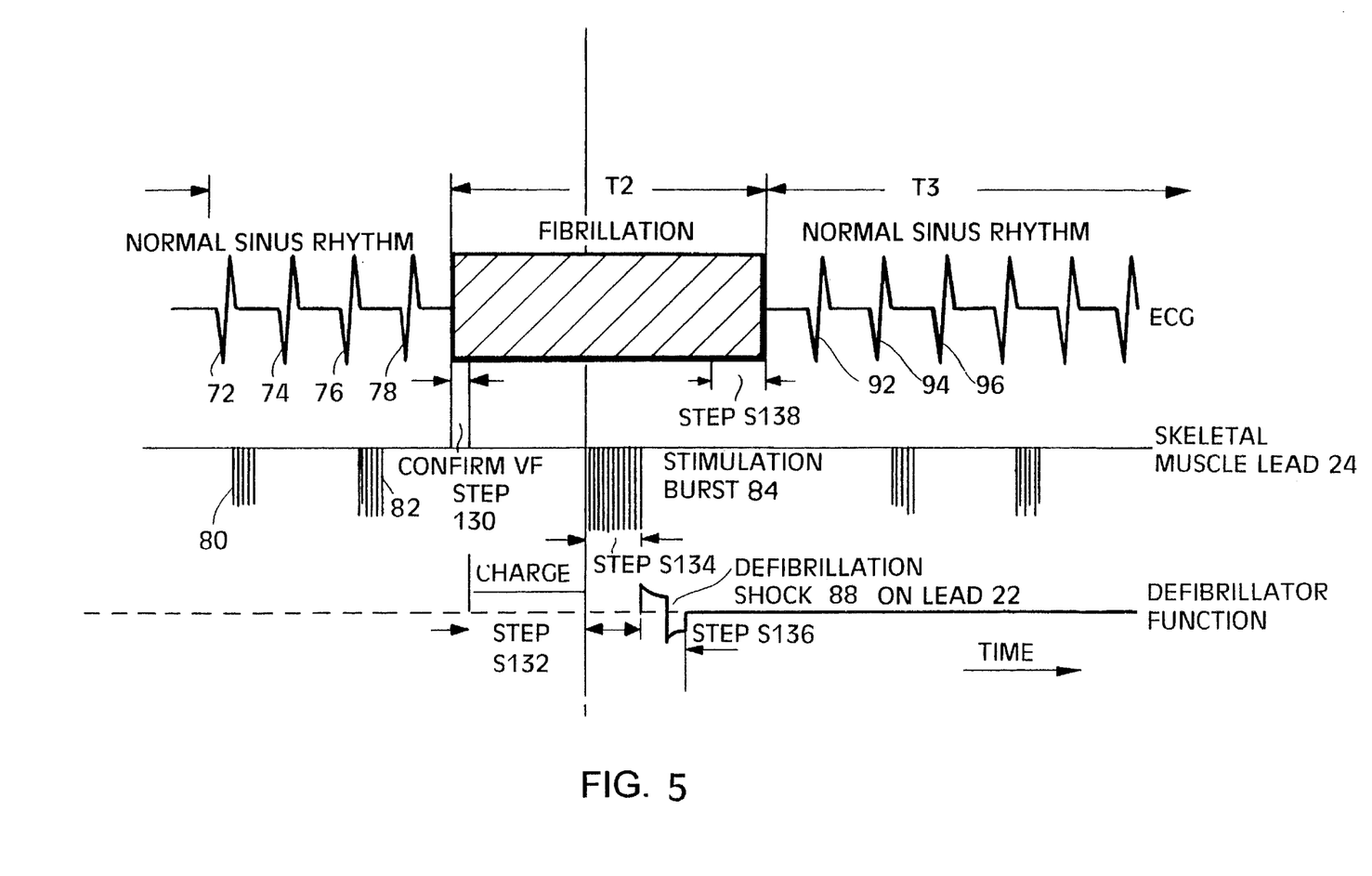
FIG. 5 shows an ECG for the patient with the corresponding defibrillation and skeletal muscle stimulation signals for the pacemaker system of FIG. 1.

Going back to step S102, if the cardiac functions not normal, in step S104 the microprocessor checks for arrhythmia. If arrhythmia is detected, in step S106 the arrhythmia is confirmed and classified. As part of this classification, the microprocessor checks for ventricular fibrillation, in step S124. For other types of arrhythmia, appropriate therapy is provided in step S108. If ventricular fibrillation is detected in step S124, the microprocessor enters into a defibrillation mode. Signals characterizing the operation of pacemaker system 10 in this mode are shown in FIG. 5. More specifically, the top row of FIG. 5 shows the ECG for heart 14. For illustrative purposes, during an initial time period T1, and a final period T3, the heart 14 is shown beating normal at its intrinsic or natural sinus rhythm, as indicated by the ECG pulses 72, 74, 76, 78, and 92, 94, 96. During the intermediate time period T2, the pacemaker system goes into the defibrillation mode during which the heart undergoes, and is treated for, ventricular fibrillation.

The second row of FIG. 5 shows the stimulation signals on skeletal muscle lead 24. During time period T1, bursts of signal such as at 80 and 82 are applied on skeletal muscle stimulation lead 24 to augment the normal cardiac function of the heart as previously discussed. As seen in FIG. 5, burst 80 is applied synchronously with pulse 72, burst 82 is applied synchronously with pulse 76 and 80, and so on. No bursts are applied during pulses 74 and 78 to allow the muscle 16 to rest.

The third row of FIG. 5 shows activities related to the defibrillation function.

At the end of time period T1, heart 14 undergoes ventricular fibrillation. This condition is detected in step 124. In step S130 the microprocessor confirms that the heart is experiencing ventricular defibrillation. Because fibrillation signals are high energy signals, the defibrillator 28 needs some initialization time during which its energy storage device 29 is charged up. This is accomplished in step S132. After the energy storage element is charged up, in step S134, the microprocessor 26 generates control signals on bus 32, in response to which the skeletal muscle stimulator generates an extended burst of signals 84 on line 24. However as opposed to bursts 80 and 82, burst 84 is not designed to augmented the cardiac function of the heart 14 and is not synchronous with its beats. Instead, this burst 84 is applied to the muscle 16 to cause the muscle to contract about the heart in order to force the blood from the cardiac chambers to be expelled. Preferably, as shown in FIG. 5, the amplitude of the signals forming burst 84 is somewhat larger than the amplitude of bursts 80, 82. In addition, the duration of the burst 84 is also somewhat longer. Immediately following burst 84, in step S136, the defibrillator 28 generates a defibrillating high energy shock signal 88 on lead 22. Because the blood was substantially ejected from the heart chambers in step S134, the full impact of shock signal 88 is applied to the heart muscles to stop the ventricular fibrillation.

In step S138, the microprocessor monitors the heart 14 for a preselected period to determine if the fibrillation has stopped and the heart has resumed its normal sinus rhythm. If normal cardiac function is resumed, as indicated by period T3, the microprocessor returns to the normal pacing mode of operation. Otherwise, step S140 orders the defibrillation therapy of period T2 (i.e. steps S130–138) to be repeated. If necessary, the amplitude, and the energy content of the defibrillation shock signal may be increased for this second defibrillation therapy.

In this manner, the subject pacemaker system provides a plurality of functions including pacing, arrhythmia therapy, cardiac function augmentation using cardiomyoplasty. In addition, if heart fibrillation is detected, defibrillation is provided, consisting of the steps of expelling the blood from the heart chambers, and then applying defibrillation shocks. Because the shocks are not partially dissipated in extraneous blood within the heart chambers, the defibrillating shocks have a lower amplitude and/or energy content than in other prior art devices. As a result, the defibrillation therapy provided by the subject system is safer for the patient and is more energy efficient.

Although the invention has been described with reference to a particular embodiment, it is to be understood that this embodiment is merely illustrative of the application of the principles of the invention and that the same objectives may be accomplished by other means as well. For example, a muscle, another biocompatible mechanical member may be wrapped about the heart, which member may be selectively contracted and extended as required to eject blood from the heart prior to defibrillation therapy. Accordingly, the embodiment described in particular should be considered exemplary, not limiting, with respect to the following claims.

We claim:

1. A heart defibrillator for defibrillating a heart, said heart being filled with a volume of blood, said heart defibrillator comprising:

means for generating a defibrillation request;

means for effecting defibrillation therapy in response to said defibrillation request;

means external of a patient's heart for selectively ejecting said volume of blood from said heart; and means for activating said blood ejecting means just prior to operation of said generating means to minimize said volume of blood during defibrillation therapy to maximize the effects of said therapy.

2. The defibrillator of claim 1 wherein said effecting means includes an energy storage device for generating shock signals, said energy storage device being charged before said blood ejecting means is activated.

3. The defibrillator of claim 2 wherein said activating means activates said generating means to send said shock signals to said heart after said blood ejecting means is activated for a preselected time period.

4. The defibrillator of claim 1 wherein said blood ejecting means includes a muscle surgically wrapped about said heart and muscle stimulating means for selectively applying muscle stimulating signals responsive to commands from said activating means for causing said muscle to contract about said heart to eject blood from the heart.

5. A pacemaker system for stimulating a patient's heart, said heart having cardiac functions for pumping blood and being associated with a skeletal muscle for augmenting the cardiac functions of the heart, said system comprising:

muscle stimulation means for selectively stimulating said muscle in response to commands;

control means for generating said commands for said muscle stimulation means, said control means having a first operational mode during which said commands are generated by said control means synchronously with a heart rate, and a second mode activated when said heart is in a fibrillation, in said second mode said control means generating said commands asynchronously with said heart rate for stimulating said muscle to eject substantially said blood from a heart chamber; and defibrillating means for defibrillating said heart, said defibrillating means being activated by said control means in said second mode to provide defibrillation therapy, said control means generating said commands for stimulating said muscle just prior to said defibrillation therapy.

6. The system of claim 5 wherein said chamber is a ventricle.

7. The system of claim 5 wherein said defibrillating means includes energy storage means for storing energy.

8. The system of claim 7 wherein said energy storage means generates shock pulses for defibrillating said heart, said shock pulses being applied after said muscle has been stimulated.

9. The system of claim 5 further comprising pacing means for generating pacing pulses for said heart, said pacing pulses defining said heart rate.

10. The system of claim 9 wherein said pacing means and said muscle stimulating means are activated synchronously by said control means.

11. An implantable defibrillator pacemaker assembly for stimulating a heart containing blood and having heart chambers, said heart being associated with a muscle surgically arranged about said heart, said assembly comprising:

a pulse unit including pacing means for generating one of a first command and a second command, said first command being related to a heart rate, and said second command being independent of said heart rate; muscle stimulating means for stimulating said muscle in response to said first command to augment a cardiac function of said heart, said muscle stimulating means stimulating said muscle in response to said second command to eject substantially said blood from said heart chambers; and defibrillating means for generating defibrillating signals for said heart said muscle being stimulated by said muscle stimulating means just prior to said defibrillating signals; and lead means for coupling said pulse unit to said heart and said muscle.

12. The system of claim 11 wherein said lead means includes a cardiac lead connecting said pacing means to said heart, a muscle stimulating lead connecting said muscle stimulating means to said muscle and a defibrillating lead connecting said defibrillating means to said heart.

13. The system of claim 12 wherein said pacing means further generates heart pacing signals, said heart pacing signals being transmitted to said heart through said cardiac lead to define said heart rate.

14. The system of claim 11 wherein said heart rate is an intrinsic heart rate.

15. The system of claim 11 wherein said defibrillating means includes an energy storage device for storing energy, said storage device generating high energy shocks for defibrillating said heart, said shocks being transmitted to said heart after said muscle is stimulated.

16. A method of defibrillating a heart, said heart containing blood, having heart functions and a chamber and being provided with a muscle for augmenting said heart functions, said method comprising the steps of:

ejecting substantially said blood from said chamber just prior to said heart being fibrillating; and applying defibrillating shock signals to the heart after said blood has been substantially ejected.

17. The method of claim 16 wherein said blood is expelled by stimulating said muscle with electrical signals.

18. The method of claim 17 wherein said heart has a fibrillated and a non-fibrillated state and wherein said muscle is stimulated at regular intervals in said non-fibrillated state for augmenting said cardiac functions.

19. The method of claim 18 wherein said heart is in said non-fibrillate state, said regular intervals being related to the heart rate.

20. The method of claim 19 further comprising pacing said heart in said non-fibrillated state to define said heart rate.

* * * * *